United States Patent [19]

Hay et al.

[11] Patent Number: 5,013,542

[45] Date of Patent: May 7, 1991

[54] METHOD TO INHIBIT ADHESION OF DISEASE-CAUSING MICROORGANISMS TO TEETH

[75] Inventors: Donald I. Hay, Wayland; Ronald J. Gibbons, Boston; Edgard G. Moreno, Nahant, all of Mass.

[73] Assignee: Forsyth Dental Infirmary for Children, Boston, Mass.

[21] Appl. No.: 153,084

[22] Filed: Feb. 8, 1988

[51] Int. Cl.$^5$ ............................................. A61K 37/18
[52] U.S. Cl. ....................................... 424/54; 514/12; 514/21
[58] Field of Search ....................... 424/54; 514/12, 21

[56] References Cited

U.S. PATENT DOCUMENTS

| Re. 31,181 | 3/1983 | Kleinberg . | |
|---|---|---|---|
| 4,225,579 | 9/1980 | Kleinberg . | |
| 4,314,991 | 2/1982 | Sipos | 424/56 |
| 4,612,190 | 9/1986 | Sato et al. . | |

FOREIGN PATENT DOCUMENTS 1200506 2/1986 Canada .
1212627 10/1986 Canada .
0203359 4/1986 European Pat. Off. .

OTHER PUBLICATIONS

Gibbons et al., Inf. & Immun., Feb. 1988, pp. 439-445.
Schlesinger and Hay, "International Journal Peptide Protein Research", 17, 1981, 34-41.

Primary Examiner—Howard E. Schain
Assistant Examiner—Choon Park Koh
Attorney, Agent, or Firm—Richard P. Crowley

[57] ABSTRACT

A composition and method for the inhibiting of adhesion of disease-causing microorganisms, such as *Streptococcus mutans*, to tooth surrfaces, which composition contains as an active ingredient a non-immunogenic amino acid segment of a proline rich protein and which method comprises treating a calcium-containing mineral surface, such as a tooth surface, with the composition.

16 Claims, No Drawings

METHOD TO INHIBIT ADHESION OF DISEASE-CAUSING MICROORGANISMS TO TEETH

BACKGROUND OF THE INVENTION

It is well known that the adhesion of disease-causing microorganisms, such as *Streptococcus mutans*, to tooth surfaces results in dental plaque formation and leads to dental diseases, including dental caries and periodontal diseases. Therefore, it is desirable to provide compositions and techniques for the prevention of adhesion of such microorganisms to surfaces of the mouth. It has been disclosed that certain anionic, aromatic polyamino acid sulfonates as active ingredients in various dental compositions are effective in inhibiting the deposition of dental plaque onto tooth surfaces (see U.S. Pat. No. 4,314,991, issued Feb. 9, 1982). Also, it has been reported that acidic phosphoproteins or polypeptides, such as casein, polyglutamate lactalbumin and polyaspartate reduce the adhesion of *Streptococcus mutans* to apatitic surfaces and thus may inhibit dental caries (see Canadian patents 1,200,506 issued Feb. 11, 1986 and 1,212,627 issued Oct. 14, 1986). The acidic polypeptides reported in the Canadian patents are derived from bovine dairy products and are immunogenic in humans. Further, a peptide with a defined amino acid sequence derived from the parotid gland of rats has been found to have a dentinal fluid transport (DFT) stimulating affect in preventing dental caries (see European patent application 86 10 5534.1, published Mar. 12, 1986, No. 0 203 359). The destruction of tooth tissues due to microorganisms has been reported to be slowed also by the use of various polypeptides having 2-4 amino acid units of at least one of which is arginine (see U.S. Pat. No. 4,225,579 issued May 15, 1979 and Re-issue U.S. Pat. No. 31,181, issued Mar. 15, 1983). A growth inhibitor for *Streptococcus mutans* has also been disclosed being a dihydro quaiaretic acid (see U.S. Pat. No. 4,612,190, issued Sept. 16, 1986). Therefore, it is desirable to treat tooth surfaces in such a way that colonization of teeth by disease-causing microorganisms is changed to the advantage of the host. Development of compositions and methods to prevent or inhibit the adhesion of disease-causing microorganisms is desirable.

The invention disclosed herein was supported in part by grants from the United States Public Health Service through the National Institute of Dental Research and National Institute of Health of Bethesda, Maryland, Grant Nos. DE 7009 and DE 8601.

SUMMARY OF THE INVENTION

The present invention relates to compositions containing as an active ingredient certain non-immunogenic amino acid segments of proline-rich proteins derived from human saliva and to a method of treating mineral surfaces, such as hydroxyapatite surfaces, for example, human tooth surfaces, to inhibit the adhesion of disease-causing microorganisms to such surfaces.

It has been found that amino acid segments of human proline-rich protein unexpectedly and strongly limit the adhesion of disease-causing microorganisms to hydroxyapatite surfaces in vitro. The amino acid segment may be obtained from acidic, proline-rich proteins, such as those derived from human saliva. These proline-rich proteins show marked charge and structural asymmetry and show exceptional reactivity to apatitic surfaces, and when intact, also promote the adhesion of microorganisms to apatitic surfaces. Because they are derived from human proline-rich proteins, they are recognized as "self" by humans, and antibodies to them have not been reported in humans. While not wishing to be bound by any theory or function or operation, it appears that part of the protein molecule reacts with the hydroxyapatite surfaces, while other parts of the protein molecule contain the active sites to which bacteria adhere. The mineral-binding segments may be used as the active ingredients alone or in combination with the other compounds, such as enzymes, antimicrobial agents, etc., in various compositions used for the treatment of the teeth so as to limit the adhesion and/or growth of microorganisms.

The active ingredient may be derived from segmenting a natural or synthetic, proline-rich protein, particularly to provide a non-immunogenic ingredient in comparison to the use of other ingredients, such as polyaspartate, which will be immunogenic in humans and thus be not wholly acceptable in use. The non-immunogenic amino acid segment may be obtained by various techniques, such as by the production of analogs of the natural proline-rich molecules or their segments by biological means, that is, by cloning, or by synthesizing analogs of the natural molecules or their segments by chemical means. In one preferred embodiment, the non-immunogenic amino acid segment is obtained by enzymatically or otherwise cleaving the proline-rich protein derived from human saliva, that is, a natural protein, by the enzyme trypsin at a particular junction, for example, at ARG segment, so as to provide a highly acidic, 30-residue, amino-terminal segment of the proline-rich protein molecule as the active ingredient. The portion of the proline-rich protein thus removed is that portion which contains the bacterial binding sites. Thus, the active ingredient of the invention should comprise the bulk of the amino acid segments of the proline-rich protein from which the active ingredient is derived. A variety of human, proline-rich phospho proteins may be employed, but particularly those proline-rich proteins which have been fully characterized to date (PRP-1,2,3,4, PIF-s, PIF-f) and others which are not fully characterized and wherein about the first 30-residue amino-terminal segment is removed and recovered.

The amino-terminal segment has not been reported to be immunogenic in humans and may be compounded, admixed or treated so as to be applied in or admixed with various pharmaceutically acceptable carriers, such as water or other inert ingredients, in a topical treating solution so that it may be applied to the teeth, or through the use of the active ingredient in mouthwashes, dentifrices, gels or in composition by being applied directly the dentist or dental technician to the tooth surface, bone, gum or surface to be protected. The 30-residue amino-terminal segment of PRP-1 derived from human saliva has been found to be particularly effective against a wide host of disease-causing microorganisms in vitro. Disease-causing microorganisms, particularly diseases which include prominent plaque species, have been found to have limited adhesion to tooth surfaces when the tooth surface has been treated with the highly acidic amino-terminal segment. Such microorganisms include, but are not limited to: *Streptococcus mutans, Streptococcus sanguis, Streptococcus sobrinus, Actinomyces viscosus*; and *Bacteroides gingivalis*. The structure of some proline-rich proteins (PRP-1,2,3,4, PIF-s, PIF-f) and the cleavage of such proline-rich proteins is described for example in the publication Schlesigner and Hay, "International Journal of Peptide Protein Research", 17, 1981, 34–41 hereby incorporated by reference. As to the other fully characterized proline-rich proteins, they range in chain length from 106 to 150 units. While the natural proline-rich proteins may vary in minor ways, they all contain highly acidic amino acid segments useful as active ingredients in the invention. Thus, all such proline-rich proteins and those analogous, structurally similar proteins may be used in deriving the active ingredients of the invention for use in the treatment of teeth surfaces.

The amino acid sequence established of proline-rich protein-1 derived from human saliva is illustrated in the attached diagram wherein the light shaded circles represent negatively charged residues and the dark circles represent positively charged residues and wherein in the preparation of the active ingredient, the 30-residue amino-terminal segment is enzymatically cleaved by trypsin abt ARG(30) to provide the very highly acidic phosphocontaining amino acid active ingredient useful for treating tooth surfaces.

While the composition and the method have been directed in particular to the treatment of tooth surfaces, that is hydroxyapatite surfaces or calcium-containing mineral surfaces for the inhibiting of disease-causing microorganisms, it is

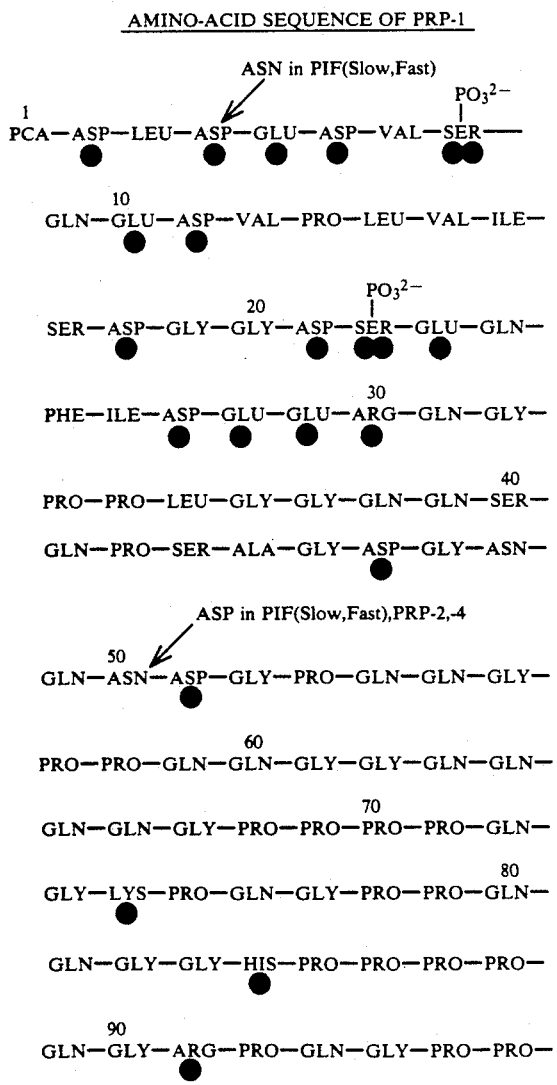

AMINO-ACID SEQUENCE OF PRP-1 also recognized that within the spirit and scope of the invention that the composition may be used to treat any mineral-containing surfaces, such as bone surfaces, ceramic surfaces or plastics, including those used for soft contact lenses for eyes, so as to aid in the insertion of artificial implants for use in ceramic and other calcium-containing particles in a coating or in the reduction of disease-causing microorganisms on joints, bones or eyes through the treating of the surfaces with natural, non-immunogenic segments so as to prevent the disease-causing micoorganisms from binding.

The invention will be described for the purposes of illustration only in connection with certain illustrative examples and embodiments. However, it is recognized that various changes, modifications, additions and improvements may be made to the illustrative embodiments by those persons skilled in the art all falling within the spirit and scope of the invention.

DESCRIPTION OF THE EMBODIMENTS

1. Preparation of specific molecular segments (peptides) from the acidic, proline-rich proteins (PRP).

The amino-acid sequences (primary structure) of six of the proline-rich proteins (PRP) have been determined. As an example, the structure of PRP-1 has been shown in the accompanying diagram. Other PRP vary in the nature of residues 4 and 50. Three PRP are 150 residues long, the other three are 106 residues long.

Studies have shown that PRP adsorb strongly to hydroxyapatite (HA, the model mineral for dental enamel), and that the part of the molecule which is important in this adsorption is the acidic (negatively charged), phosphoserine-containing.(residues 8 and 22) segment from residue 1 to at least residue 30. This molecular segment can be separated from the rest of the molecule, such as by treatment with an enzyme. Trypsin is a suitable enzyme because it only cleaves the bonds between arginine (ARG) and lysine (LYS) and the next amino-acid in the sequence. Thus, the bond between residues 30 and 31 would be cleaved and the

RELATIVE ADHESION OF BACTERIA TO APATITIC SURFACES

| ORGANISM | ASSOCIATED PROPERTY | PERCENT ADHESION COMPARED TO SALIVA-TREATED HA HA-TREATED WITH | |
|---|---|---|---|
| | | PRP-1 | PRP-1(T1) |
| *Streptococcus mutans* | Caries etiology | 81 | 17 |
| *Streptococcus mitis* | Plaque formation | 38 | 26 |
| *Streptococcus sanguis* | Plaque formation | 144 | 4 |
| *Actinomyces viscosus* | Root caries | 105 | 17 |
| *Bacteroides gingivalis* | Periodontal disease | 335 | 20 | molecular segment residues 1-30 obtained, amongst others. This peptide from PRP-1 is designated as PRP-1(Tl), to define it as the first peptide in the sequence obtained by tryptic digestion. Because PRP-1(Tl) is strongly negatively charged, it can be separated from the other peptides and trypsin by passing the mixture through a column of a positively charged material such as diethylaminoethyl (DEAE) agarose designed for this purpose and available from commercial sources. PRP-1(Tl) binds to the positively charged DEAE groups and the other peptides and trypsin can be washed away. PRP-1(Tl) is then dissociated from the DEAE agarose with a suitable salt, such as ammonium bicarbonate, at progressively increasing concentrations, until the peptide is recovered. The recovered peptide is then analyzed for its constituent amino-acids to confirm that pure PRP-1(Tl) has been obtained. These procedures are more fully described in Schlesinger, D.H. and Hay, D.I., "International Journal of Peptide Protein Research", Vol. 17, 1981, pp. 34–41.

2. Adhesion of bacteria to PRP and PRP-1(Tl) adsorbed onto HA.

PRP-1 and PRP-1(Tl) were investigated for their abilities to promote adhesion of bacteria to HA. Essentially, the method is to treat HA samples with nothing (negative control), saliva (positive control), or the respective proteins or peptides. The excess agent is removed by washing, and suspensions of radioactively labeled bacteria are added to the treated HA. After a suitable time, the excess bacteria are removed by washing and those remaining adsorbed to the HA are counted in a scintillation counter. In the table of results, bacterial adsorption to saliva-treated HA is considered to be 100%, and adsorption to PRP-1 or PRP-1(Tl)-treated HA expressed as a percentage of this reference value. This approach is necessary because of the diverse behaviors of different bacteria.

The profound effect of PRP-1 and PRP-1(Tl) on bacterial adhesion is clearly seen. In some cases adhesion to PRP-1 was less than or equal to adhesion to saliva-treated HA. In two cases (*S. sanguis* and *B. gingivalis*), adhesion to PRP-1-treated HA was higher than adhesion to saliva-treated HA, showing the importance of the PRP for the adhesion of these organisms. In all cases, however, adhesion of these organisms was significantly and profoundly depressed when the HA was treated with the PRP-1(Tl) segment. Thus, the amino-terminal segments of proline-rich protein may be used as active ingredients in a composition for the treatment of a mineral surface to prevent or inhibit the adhesion of disease-causing microorganisms, and consequently to reduce incidence of such diseases, particularly in the oral cavity.

What is claimed is:

1. A method of inhibiting the adhesion of microorganisms to a mineral surface, which method comprises:
   contacting the mineral surface with an adhesive-inhibiting amount of a non-immunogenic, acidic, amino-terminal segment of an anionic proline-rich protein to inhibit the adhesion of disease-causing microorganisms to the mineral surface.

2. The method of claim 1 wherein the mineral surface comprises a manual calcium-containing surface.

3. The method of claim 1 wherein said mineral surface comprises hydroxyapatite.

4. The method o claim 1 wherein the mineral surface comprises a tooth surface.

5. The method of claim 1 wherein the anionic proline-rich protein comprises PRP 1-4, PIF-s or PIF-f.

6. The method of claim 1 which includes cleaving the proline-rich protein by enzymatic cleaving to obtain the acidic amino acid end segment of the protein and contacting the mineral surface with said cleaved amino-terminal segment.

7. The method of claim 1 wherein said segment consists essentially of the first 30 amino-acid residue of the said protein.

8. The method of claim 1 wherein said end segment comprises PCA—ASP—LEU—ASP—GLU—ASP—VAL—P-Ser—GLN13 GLU—ASP—VAL—PRO—LEU—VAL—ILE—SER—ASP—GLY—GLY—ASP—P-SER—GLU—GLN—PHE—ILE—ASP—GLU—GLU—ARG.

9. The method of claim 1 which includes incorporating the said segment in a pharmaceutically acceptable carrier to form a composition and treating an apatitic surface of a patient with said composition.

10. The method of claim 9 which includes treating the oral cavity of a patient with said composition.

11. The contacted mineral surface prepared by the method of claim 1.

12. A method of inhibiting the adhesion of disease-causing microorganisms, which method comprises:
   a) providing as an active ingredient a non-immunogenic peptide consisting essentially of the first acidici 30-residue amino-terminal segment of a proline-rich protein;
   b) incorporating the said segment in a pharmaceutically acceptable carrier to form a composition; and
   c) introducing the said composition into the oral cavity of a patient.

13. The treated oral cavity prepared by the method of claim 12.

14. The method of claim 1 which includes cleaving the proline-rich protein by enzymatic cleaving by the use of trypsin.

15. The method of claim 1 wherein the disease causing microorganisms are selected form the group consisting of: Streptococcus mutans, Streptococcus sanguis, Streptococcus sobrinus, Actinomyces viscosus and Bacteroides gingivalis.

16. The method of claim 12 wherein the 30 residue amino terminal segment of a proline-rich protein comprises: PCA—ASP—LEU—ASP—GLU—AS-P—VAL—P-SER—GLN—GLU—ASP—VAL—PRO—LEU—VAL—ILE—SER—ASP—GLY—GLY—ASP—P-SER—GLU—GLN—PHE—ILE—ASP—GLU—GLU—ARG.

* * * * *

UNITED STATES PATENT AND TRADEMARK OFFICE
CERTIFICATE OF CORRECTION

PATENT NO. : 5,013,542
DATED : May 7, 1991
INVENTOR(S) : Hay et al

It is certified that error appears in the above-identified patent and that said Letters Patent is hereby corrected as shown below:

Col. 6, line 22 (Claim 2), delete "manual" and insert --mammal--.

Signed and Sealed this

Fifteenth Day of September, 1992

*Attest:*

DOUGLAS B. COMER

*Attesting Officer*   *Acting Commissioner of Patents and Trademarks*